(12) United States Patent
Estevez et al.

(10) Patent No.: US 12,096,935 B2
(45) Date of Patent: Sep. 24, 2024

(54) SYSTEMS, DEVICES, AND RELATED METHODS FOR FASTENING TISSUE

(71) Applicant: Boston Scientific Scimed, Inc., Maple Grove, MN (US)

(72) Inventors: Ramon Estevez, Lowell, MA (US); Christopher Deuel, Melrose, MA (US); Paul Smith, Smithfield, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 276 days.

(21) Appl. No.: 17/652,800

(22) Filed: Feb. 28, 2022

(65) Prior Publication Data

US 2022/0280158 A1 Sep. 8, 2022

Related U.S. Application Data

(60) Provisional application No. 63/156,027, filed on Mar. 3, 2021.

(51) Int. Cl.
*A61B 17/072* (2006.01)
*A61B 17/00* (2006.01)

(52) U.S. Cl.
CPC ........... *A61B 17/07207* (2013.01); *A61B 2017/00367* (2013.01); *A61B 2017/07257* (2013.01); *A61B 2017/07278* (2013.01)

(58) Field of Classification Search
CPC ...... A61B 17/07207; A61B 2017/0034; A61B 2017/00367; A61B 2017/07257; A61B 2017/07278; A61B 1/00087
USPC .............................. 227/175.1, 176.1, 180.1
See application file for complete search history.

(56) References Cited

U.S. PATENT DOCUMENTS

| | | | | |
|---|---|---|---|---|
| 8,490,851 B2 * | 7/2013 | Blier | ............ | A61B 17/068 227/176.1 |
| 2003/0045900 A1 | 3/2003 | Hahnen et al. | | |
| 2005/0006432 A1 * | 1/2005 | Racenet | ............ | A61B 17/105 227/176.1 |
| 2005/0256533 A1 * | 11/2005 | Roth | ............ | A61F 5/0083 606/167 |
| 2007/0167960 A1 * | 7/2007 | Roth | ............ | A61B 17/072 606/153 |
| 2008/0035701 A1 * | 2/2008 | Racenet | ............ | A61B 17/07207 227/176.1 |
| 2013/0304097 A1 * | 11/2013 | Blier | ............ | A61B 17/068 606/144 |
| 2016/0192927 A1 * | 7/2016 | Kostrzewski | ...... | A61B 17/0643 227/176.1 |
| 2016/0256152 A1 * | 9/2016 | Kostrzewski | ...... | A61B 17/42 |

(Continued)

*Primary Examiner* — Valentin Neacsu
(74) *Attorney, Agent, or Firm* — Bookoff McAndrews, PLLC

(57) ABSTRACT

According to one aspect, a tissue fastening device may include a first body including a proximal end, a distal end, and defining a longitudinal axis; and a fastening device coupled to the distal end of the first body. The fastening device may include a longitudinal body comprising a cartridge; the cartridge configured to hold one or more fasteners; an anvil rotatable relative to the cartridge of the longitudinal body; a fastener actuator configured to move relative to the cartridge to deploy the one or more fasteners from the cartridge; and an actuation wire coupled to the fastener actuator, extending through the first body, and positioned at least partially exterior to the longitudinal body, the cartridge, or the anvil.

17 Claims, 3 Drawing Sheets

(56) References Cited

U.S. PATENT DOCUMENTS

| | | | |
|---|---|---|---|
| 2020/0275925 A1* | 9/2020 | Smith | A61B 1/00137 |
| 2021/0007736 A1* | 1/2021 | Smith | A61B 17/0686 |
| 2021/0022720 A1* | 1/2021 | Smith | A61B 17/00234 |
| 2021/0022733 A1* | 1/2021 | Smith | A61B 17/0686 |
| 2021/0236120 A1* | 8/2021 | Estevez | A61B 17/0686 |
| 2021/0275168 A1* | 9/2021 | Smith | A61B 17/07207 |
| 2022/0280158 A1* | 9/2022 | Estevez | A61B 1/00087 |
| 2023/0397908 A1* | 12/2023 | Smith | A61B 17/00234 |

* cited by examiner

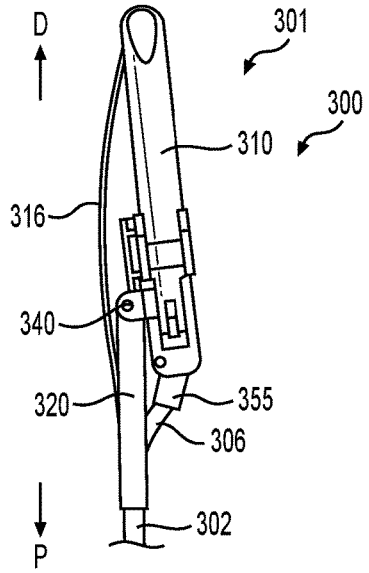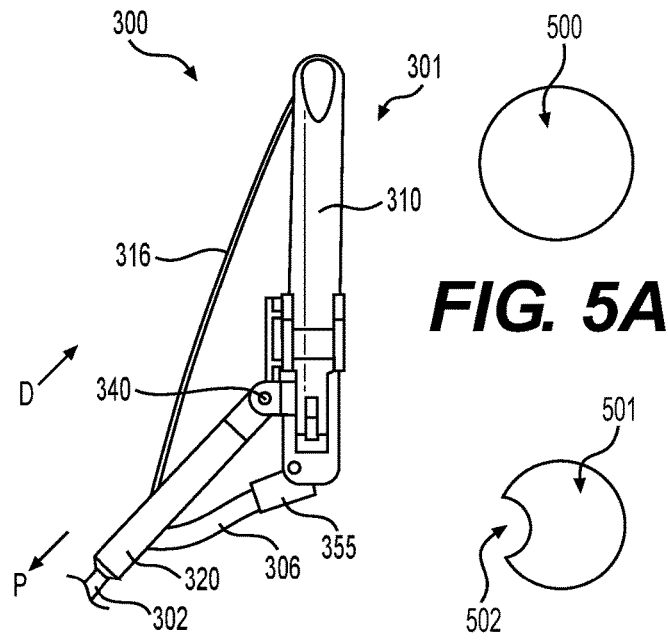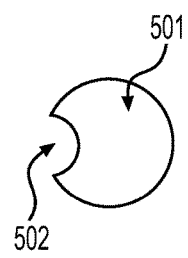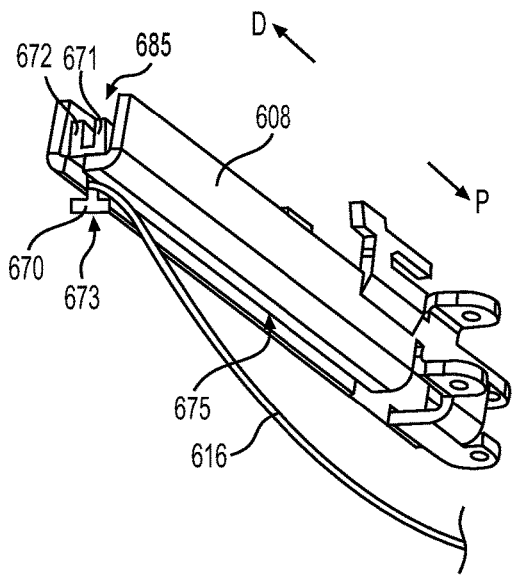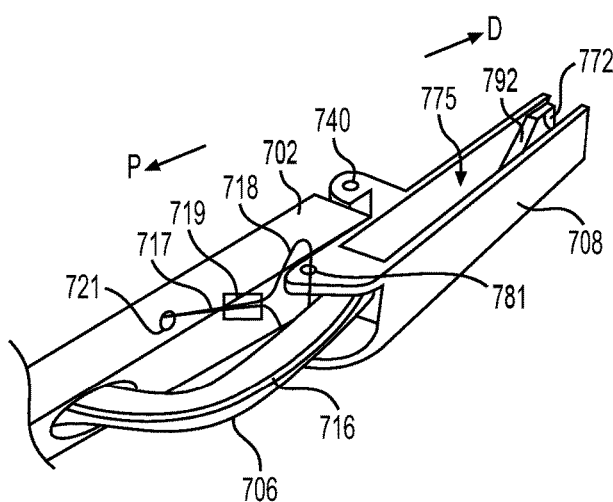
FIG. 4A  FIG. 4B  FIG. 5A  FIG. 5B  FIG. 6  FIG. 7

SYSTEMS, DEVICES, AND RELATED METHODS FOR FASTENING TISSUE

CROSS-REFERENCE TO RELATED APPLICATION(S)

This application claims the benefit of priority of U.S. Provisional Patent Application No. 63/156,027, filed Mar. 3, 2021, the entirety of which is incorporated by reference herein.

TECHNICAL FIELD

Various aspects of the present disclosure relate generally to tissue manipulation, including visualizing, retracting, and coupling tissue. More specifically, at least certain embodiments of the present disclosure relate to systems, devices, and related methods for fastening tissue, among other aspects.

BACKGROUND

Technological developments have given users of medical systems, devices, and methods, the ability to conduct increasingly complex procedures on subjects. The coupling of tissue in, for example, a subject's gastrointestinal tract, is a type of procedure in which difficulties may arise. Surgical devices may grasp or clamp tissue between opposing jaw structures and then join the tissue by surgical fasteners.

Some actuators in surgical staplers include pulling or pushing a wire through the device. When the stapler is positioned within a tortious pathway, movement of the wire through the fastening device may be difficult due to increased strain or other forces on the wire from other portions of the stapler. There is a need for systems, devices, and related methods for fastening tissue that include features that address this difficulty.

SUMMARY

Aspects of the disclosure relate to, among other things, systems, devices, and methods for fastening tissue. Each of the aspects disclosed herein may include one or more of the features described in connection with any of the other disclosed aspects.

According to one aspect, a tissue fastening device may include a first body including a proximal end, a distal end, and defining a longitudinal axis; and a fastening device coupled to the distal end of the first body. The fastening device may include a longitudinal body comprising a cartridge; the cartridge configured to hold one or more fasteners; an anvil rotatable relative to the cartridge of the longitudinal body; a fastener actuator configured to move relative to the cartridge to deploy the one or more fasteners from the cartridge; and an actuation wire coupled to the fastener actuator, extending through the first body, and positioned at least partially exterior to the longitudinal body, the cartridge, or the anvil.

In other aspects, the fastening device may include one or more of the following features. The longitudinal body may be pivotable coupled to the first body. A longitudinal member may be coupled to a proximal end of the longitudinal body. The first body may include a first lumen extending from a proximal portion of the first body to a first lumen opening at a distal portion of the first body, and the longitudinal member and the actuation wire are at least partially positioned within the first lumen. The longitudinal member may include a longitudinal channel, and the actuation wire may be positioned within the longitudinal channel. The first body may include a second lumen opening into the first lumen; and the first lumen opening may be positioned at an opposite side of the first body from the second lumen opening. The first body may include a first lumen and a second lumen; the longitudinal member may be positioned within the first lumen; and the actuation wire may be positioned within the second lumen.

In other aspects, the fastening device may include one or more of the following features. The fastener actuator may be positioned within a longitudinal slot of the longitudinal body. The fastener actuator may include at least one ramp portion and an extension portion extending through the longitudinal slot. A spring may be coupled to the first body and the longitudinal body. The spring may be configured to bias the fastening device towards a positioned in which a longitudinal axis of the longitudinal body is transverse to a longitudinal axis of the first body. The longitudinal member may be coupled to a proximal end of the longitudinal body via a coupler, and the coupler may have a width larger than the width of the first lumen opening. A cable may be rotatably coupled to the longitudinal body and positioned within the first body, and the cable may be configured to actuate movement of the fastening device. The longitudinal body may be rotatably coupled to the first body at a position between a proximal end and a distal end of the longitudinal body. Longitudinal member and actuation wire each may extend through at least one opening of the first body at a position entirely proximal to the fastening device.

In other aspects, a tissue fastening device may include a first body defining a longitudinal axis and including a first lumen; and a fastening device rotatably coupled to a distal end of the first body. The fastening device may include a longitudinal body; a cartridge positioned at least partially within the longitudinal body and comprising one or more fasteners; an anvil mounted adjacent the cartridge; an actuation wire coupled to a fastener actuator at a distal end of the actuation wire, wherein the fastener actuator is positioned within the channel; a second body including a second lumen, wherein the second body is positioned within, movable within, and extends from the first lumen; and a cable rotatably coupled to the longitudinal body and extending through the first lumen. The actuation wire may be positioned within the second lumen; and the fastening device may be pivotable about the first body when the cable is moved proximally and/or distally. In some examples, the first body may be rotatably coupled to the longitudinal body at a position between a proximal end and a distal end of the longitudinal body.

In other aspects, a tissue fastening device may include: a first body defining a longitudinal axis; and a fastening device rotatably coupled to a distal end of the first body. The fastening device may include a longitudinal body configured to hold one or more fasteners; an anvil rotatable relative to the longitudinal body; a fastener actuator configured to move proximally relative to the longitudinal body to deploy the one or more fasteners from the fastening device; and an actuation wire coupled to the fastener actuator, extending through the first body, and positioned at least partially exterior to the longitudinal body and the anvil.

In other aspects, the fastening device may include one or more of the following features. A spring may be coupled to the longitudinal body and the first body. A second body may be coupled to the longitudinal body and extending through the first body, and the second body may be moveable within the first body and configured to rotate the fastening device relative to the first body via proximal or distal movement of the second body.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 4A and 4B are top views of the distal end of the surgical stapler of FIG. 2, according to aspects of this disclosure.

FIGS. 5A and 5B are cross-sectional views of exemplary longitudinal members, according to aspects of the present disclosure.

FIG. 6 is a perspective view of an exemplary portion of a surgical stapler, according to aspects of the present disclosure.

FIG. 7 is a perspective view of an exemplary distal portion of a surgical stapler, according to aspects of the present disclosure.

DETAILED DESCRIPTION

The present disclosure is drawn to systems, devices, and methods for fastening tissue, among other aspects. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. The proximal and distal directions are labeled throughout the drawings with an arrow labeled "D" for the distal direction and an arrow labeled "P" for the proximal direction. The term "coupling tissue together" may refer, for example, to stapling, fixing, attaching, fastening, or otherwise joining two portions of tissue together. The term "fastener" may include staples, clips, elastic bands, suture, or any other fastener known in the art. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Embodiments of the present disclosure may be used to visualize, cut, resect, and/or couple together target tissue in an endo-luminal space, or facilitate the process thereof. In particular, some embodiments include pivotable tissue stapling devices. The stapling apparatus may be delivered to target tissue through an endoscope working channel to the target tissue site. An actuation wire may be moved through the stapling device to deploy one or more fasteners into the target tissue site. All or parts of the tissue stapling device could be metallic, plastic, or include a shape memory metal (such as nitinol), a shape memory polymer, a polymer, or any combination of materials.

Figure 1:
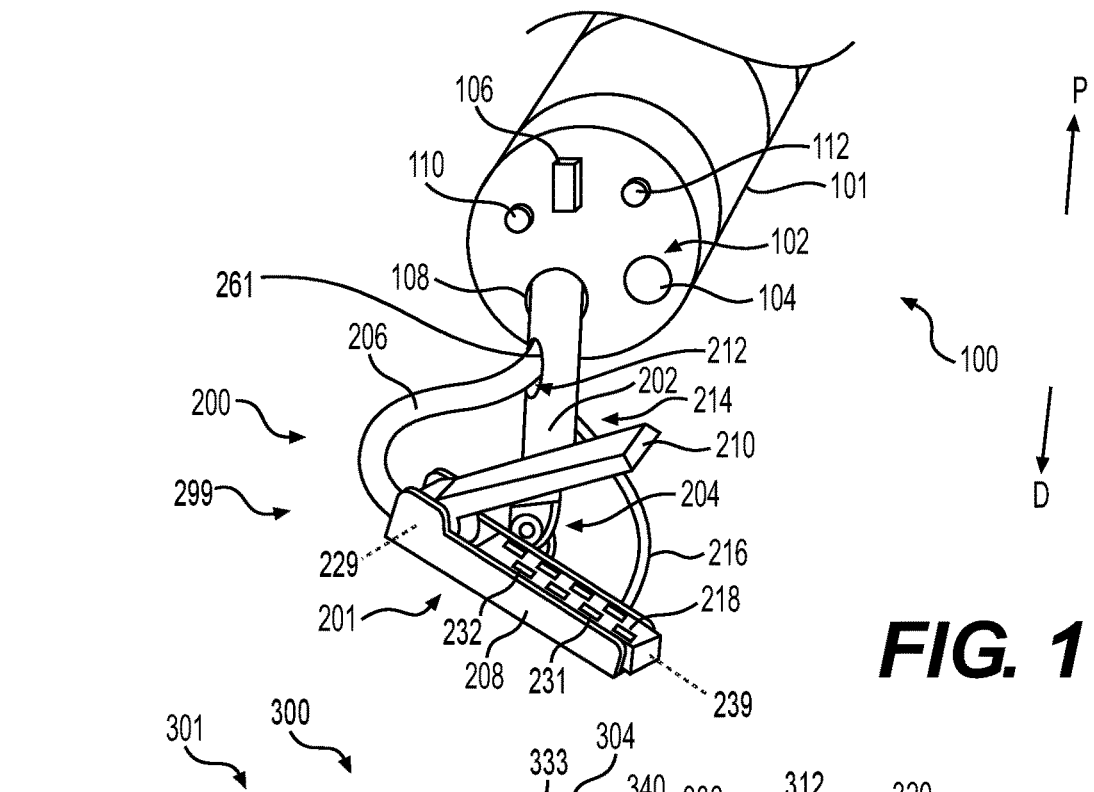
FIG. 1 is a perspective view of a distal end of an exemplary medical fastening system, according to aspects of this disclosure.

FIG. 1 shows a distal portion of a medical system 100 including an endoscope 101 and a surgical stapler 200. Endoscope 101 may include an imager 104 such as a camera, fluid channels 110, 112, an illuminator 106, and a working channel 108. A distal face 102 of endoscope 101 may include distal openings of fluid channels 110, 112, and working channel 108. Endoscope 101 may extend proximally to a handle (not shown) with one or more actuators to articulate endoscope 101 and/or actuate imager 104, illuminator 106, and/or one or more fluid channels 110, 112. Surgical stapler 200 is shown positioned within working channel 108 of endoscope 101, and surgical stapler 200 may extend proximally through endoscope 101 to a handle at a proximal end of surgical stapler 200. The handle of surgical stapler 200 may include one or more actuators for actuating one or more features of surgical stapler 200. Specific examples of handles for surgical stapler 200 or any other embodiments of surgical staplers disclosed herein are detailed in U.S. patent application Ser. No. 16/804,887, filed Feb. 28, 2020, which is incorporated by reference in its entirety.

Surgical stapler 200 is a stapling apparatus configured to engage body tissue and apply a plurality of surgical fasteners thereto in minimally invasive surgical procedures, such as laparoscopic or endoscopic procedures. In some examples, surgical stapler 200 may also form an incision in the fastened body tissue during the procedure. Surgical stapler 200 may be used to apply surgical clips or other fasteners, but will be primarily discussed in the context of applying staples from a staple cartridge positioned in a portion of the device's body, such as a loading unit.

As illustrated in FIG. 1, surgical stapler 200 includes a stapler device 201 and a longitudinal body 202. Longitudinal body 202 may extend from the stapler device 201 at a distal section 299 of surgical stapler 200 to a handle assembly (not shown) at a proximal section of surgical stapler 200. The longitudinal body 202 may extend any length suitable for endoscopic or laparoscopic procedures, and may be configured to be positioned within a working channel of an endoscope. In some examples, the longitudinal body 202 may be detachable from a handle assembly to facilitate insertion of the longitudinal body 202 into a working channel of an endoscope or a channel of another device, for example by backloading longitudinal body 202 into the working channel 108. In other examples, surgical stapler 200 may not include a handle. In some examples, the longitudinal body 202 may be flexible and/or may be rotatable about its central longitudinal axis. Longitudinal body 202 may include a lumen for positioning actuation wires within longitudinal body 202 for actuating the surgical stapler 200, and such actuation wires may be coupled to a handle assembly. Longitudinal body 202 may be configured to receive a plurality of actuation wires or a single actuation wire (for example, actuation wire 216). In some examples, the longitudinal body 202 may be fixedly coupled to the stapler device 201, and in other examples the longitudinal body 202 may be removably or releasably coupled to the stapler device 201. As shown in FIG. 1, longitudinal body 202 may be pivotably coupled to stapler device 201 via a connector 204. In some examples, connector 204 may be positioned between proximal and distal ends of a body 208 of stapler device 201. Connector 204 may be offset from a longitudinal axis 239 of the body 208 of stapler device 201.

Distal section 299 of surgical stapler 200 includes a stapler device 201 coupled to a distal portion of longitudinal body 202. In some examples, body 208 of stapler device 201 may include a cartridge 218 positioned within a channel of body 208. Cartridge 218 may be fixedly or moveably coupled to body 208 or may be removable from body 208. In some examples, cartridge 218 may be integrally formed in body 208. At a proximal portion of body 208, an anvil 210 may be rotatably or pivotably coupled to body 208 at pivot axis 229, and may extend distally towards a distal end of stapler device 201. In some examples, anvil 210 may be rotatably biased and may be biased to an open configuration, i.e. biased away from body 208 and cartridge 218 creating a space between the distal portion of anvil 210 and the distal portion of body 208 and cartridge 218. Anvil 210 may be rotatable about pivot axis 229 to contact body 208, or pinch tissue between anvil 210 and body 208, and provide a surface against which staples may be driven when ejected from cartridge 218.

In some examples, body 208 may include a channel that supports cartridge 218. Cartridge 218 may contain a plurality of surgical fasteners, such as staples, and the fasteners may be deployed from cartridge 218 when under the influence of a driving force exerted by an actuation sled, such as one of actuation sleds 673, 772 shown in FIGS. 6 and 7. A plurality of spaced apart longitudinal slots 231, 232 in cartridge 218 allow staples to pass through cartridge 218 and pierce tissue. In some examples, an actuation sled 673, 772 moves proximally in the longitudinal direction (or in a direction parallel to axis 239) from a distal end of cartridge 218 and/or body 208 when actuated, contacting fasteners within cartridge 218 and pushing fasteners through longitudinal slots 231, 232 in order to couple fasteners to tissue. In some examples, a single fastener may extend through each slot 231, 232. Each fastener may be partially within a slot 231, 232 prior to deployment to assist with alignment of the fastener with the slot 231, 232. In some examples, two actuation sleds may be required to actuate two different longitudinal rows of fasteners in cartridge 218. Alternatively, a single actuation sled 673 may include two ramp portions 671, 672, and each ramp portion 671, 672 may be aligned with a separate longitudinal row of slots 231, 232 on cartridge 218.

In some examples, cartridge 218 may also include a longitudinal slot (not shown) configured to receive and/or support a resecting tool, such as a knife blade (not shown). The resecting tool may be actuated via an additional, separate actuation wire from the actuation wire that translates the actuation sled 673, 772, or may be actuated via the same actuation wire as the actuation sled 673, 772 to translate both the actuation sled and the cutting tool at the same time. Further discussion of the use of a resecting tool with cartridge 218 may be found in U.S. patent application Ser. No. 16/804,887, filed Feb. 28, 2020.

In some examples, longitudinal body 202 may be rigid and may be coupled to a flexible body configured to pass through an endoscope or other medical device. Longitudinal body 202 may be manufactured from polyether ether ketone (PEEK), stainless steel, or other suitable materials. A longitudinal member 206 may extend within a lumen 212 of longitudinal body 202 and exit lumen 212 at a position proximal the distal end of longitudinal body 202. Lumen 212 of longitudinal body 202 may extend longitudinally from a proximal end to a distal portion of longitudinal body 202, and lumen 212 may include an exit opening 261 at a side wall of longitudinal body 202.

Longitudinal member 206 may be fixedly coupled to a proximal end of body 208. Longitudinal member 206 may be moveable within longitudinal body 202 and may exit lumen 212 through exit opening 261 at a proximal portion of surgical stapler 200. Longitudinal member 206 may be configured to move proximally and distally through lumen 212. In some examples, longitudinal member 206 may be a non-compressible member, such as a Bowden cable. Longitudinal member 206 may include a second lumen (not shown and separate from lumen 212) for receiving actuation wires and other components of surgical stapler 200.

In some examples, connector 204 permits pivoting of stapler device 201 relative to longitudinal body 202. For example, stapler device may pivot about connector 204 such that stapler device 201 may move between 1) a position where the longitudinal axis 239 of stapler device 201 is parallel with the longitudinal axis of longitudinal body 202 and 2) a position where the longitudinal axis of stapler device 201 is transverse to the longitudinal axis of longitudinal body 202. In embodiments, connector 204 may permit such pivoting so that the angle between a longitudinal axis of longitudinal body 202 and axis 239 is greater than zero degrees and up to 180 degrees when the longitudinal axis 239 of stapler device 201 is parallel with a longitudinal axis of longitudinal body 202. In some examples, exit opening 261 may be oval shaped and may be elongate in the longitudinal direction of longitudinal body 202 to allow longitudinal member 206 to smoothly transition into and out of longitudinal body 202 and to minimize friction between exit opening 261 of lumen 212 and longitudinal member 206 when longitudinal member 206 moves through lumen 212.

A user may pivot stapler device 201 by pushing or pulling on longitudinal member 206 (to move longitudinal member 206 proximally or distally), which then pushes or pulls on stapler device 201 and causes stapler device 201 to rotate about connector 204. In some embodiments, connector 204 may include a pin extending through a device at a distal end of longitudinal body 202 and a flange extending from stapler device 201. Stapler device 201 may include a pair of flanges extending from a portion of its body that include apertures for a pin, and longitudinal body 202 may include a device extending from a distal end of longitudinal body 202 including an aperture that is configured to align with the apertures of the pair of flanges, and a pin may be positioned with the apertures of the pair of flanges and the aperture of the device extending from a distal end of longitudinal body 202 to form connector 204.

An actuation wire 216 may extend from a ram actuator sled of stapler device 201 through a second lumen 214 of longitudinal body 202 to a proximal portion of stapler device 201. Actuation wire 216 may be entirely external from body 208 and anvil 210. In other examples, actuation wire 216 and longitudinal member 206 may extend through the same lumen 212. A second actuation wire may extend through longitudinal member 206 and may be configured to actuate movement of anvil 210 towards or away from body 208. In some examples, actuation wire 216 may be coupled to a handle of stapler device 201. Actuation wire 216 may be configured to move proximally or distally through a portion of longitudinal body 202, may be positioned exterior to body 208 and anvil 210, and may be coupled to a ramp actuation sled 673, 772 at least partially positioned within stapler device 201. Actuation wire 216 may be configured to actuate the deployment of fasteners from stapler device 201 by pulling ramp actuation sled 673, 772 proximally. Actuation wire 216 may enter longitudinal body 202 at a position proximal from the distal end of stapler device 201 and proximal from the distal end of longitudinal body 202.

In some examples, an actuation wire may extend through longitudinal member 206 and within body 208 and/or anvil 210, however the combination of tortuosity and stiffness of longitudinal member 206, body 208, and anvil 210 may make movement of the actuation wire through longitudinal member 206 difficult, and the positioning of actuation wire relative to body 208 and longitudinal body 202 may increase the friction experienced by movement of the actuation wire. By positioning actuation wire 216 exterior from body 208 as opposed to within body 208, it may be less difficult for a user to pull actuation wire 216 proximally because the force exerted by longitudinal member 206 on actuation wire 216 may be reduced. In addition, actuation wire 216 may be at least partially outside longitudinal member 206 and portions of longitudinal body 202. Positioning actuation wire 216 at least partially outside longitudinal member 206 and portions of longitudinal body 202 may further ease pulling actuation wire 216 proximally due to reduced loads and friction forces. By pulling actuation wire 216 proximally, an actuation sled 673 may be moved proximally and may push one or more fasteners out of cartridge 218.

A user may use surgical stapler 200 to couple one or more fasteners to tissue by first positioning tissue within the active region of stapler device 201, or between body 208 and anvil 210. Once tissue is positioned in the active region of stapler device 201, a user may actuate an actuator of a handle of stapler device 201, which may then translate an actuation wire proximally through longitudinal member 206 and cause anvil 210 to close onto the tissue positioned within the stapler device's active region. While the user holds the stapler device 201 in an engaged position, thus maintaining the stapler device's clasp on the tissue, the user may pull proximally (or actuate) on actuation wire 216 to translate an actuation sled 673 in stapler device 201. When the actuation sled 673, 772 is translated proximally via actuation wire 216, a ramp portion 671, 672, 792 of the actuation sled 673, 772 may engage a fastener in cartridge 218 and push the fastener through a longitudinal slot 231, 232 to pierce the tissue. When the fastener is deployed by the actuation sled 673, 772, the fastener may subsequently engage anvil 210 and couple layers of tissue together. In some examples, the actuation wire 216 may actuate an actuation sled and a cutting tool (not shown), and may translate both the actuation sled and the cutting tool simultaneously to both pierce and fasten tissue with one or more fasteners and cut tissue.

Figure 2:
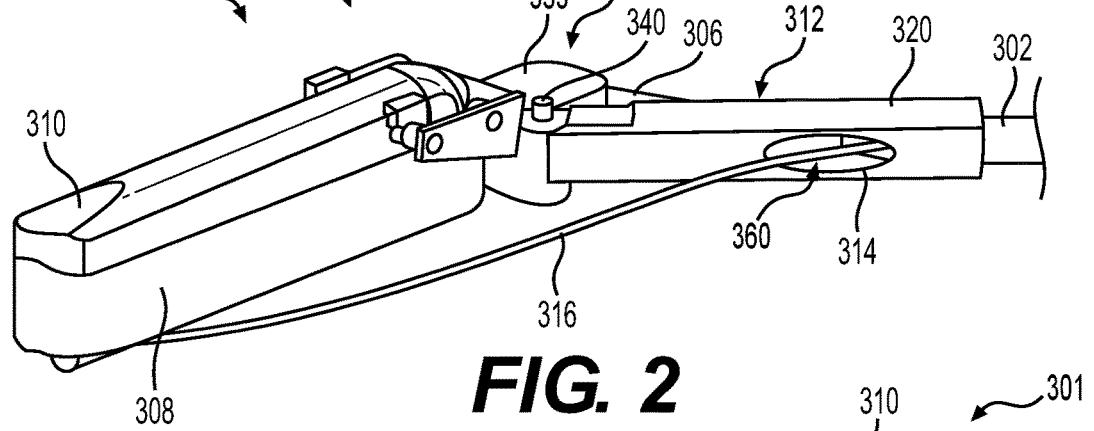
FIG. 2 is a perspective view of a distal end of an exemplary surgical stapler of a medical fastening system of FIG. 1, according to aspects of this disclosure.

FIG. 2 illustrates a distal portion of an alternative embodiment of a surgical stapler 200 including stapler device 301. Stapler device 301 may include longitudinal body 302, stapler body 308, anvil 310, longitudinal member 306, connector 304, and actuation wire 316. Surgical stapler 300 may include any of the features discussed herein regarding surgical stapler 200. Longitudinal body 302 may include a single lumen 360 and each of actuation wire 316 and longitudinal member 306 may extend through lumen 360. Longitudinal member 306 may extend through first distal opening 312 of lumen, and actuation wire 316 may extend through second distal opening 314 at an opposite side of longitudinal body 302 as first distal opening 312. Longitudinal body 302 may include a distal portion 320 including a connector 304 at a distal end of distal portion 320. Connector 304 may pivotably couple stapler device 301 to longitudinal body 302, and connector 304 may be positioned at a distal end portion of stapler device 301. Connector 304 may include a pivot pin 340, and connector 304 may be rotatable about pivot pin 340. A protrusion 333 of connector 304 may be fixedly coupled to stapler body 308 and may extend proximally relative to stapler body 308. Longitudinal member 306 may be rotatably coupled to protrusion 333 via a coupler 355. In other examples, longitudinal member 306 may be fixedly coupled to protrusion 333 via coupler 355 or any other means known in the art. Proximal or distal movement of longitudinal member 306 may cause rotation of stapler device about pivot pin 340.

Figure 3:
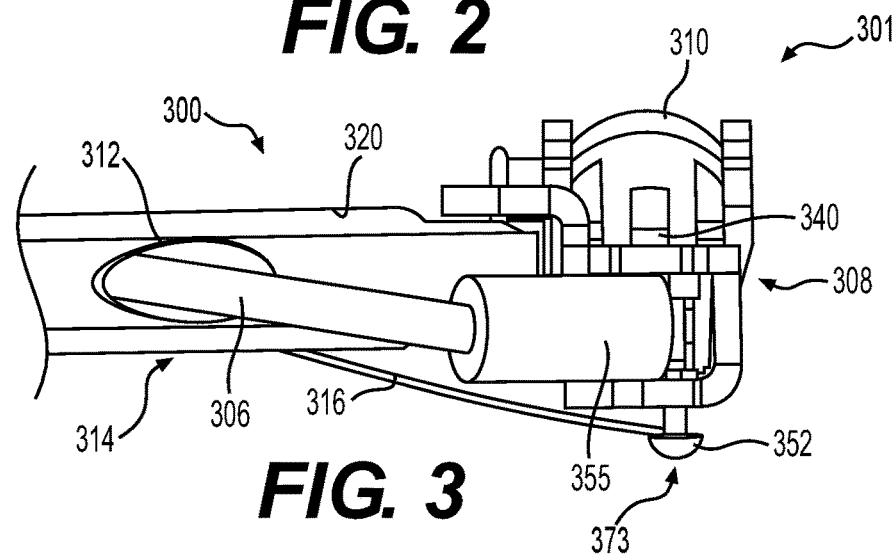
FIG. 3 is a side view of a portion of the exemplary surgical stapler of FIG. 2, according to aspects of this disclosure.

FIG. 3 illustrates a rear view of a distal portion of surgical stapler 300. As shown in FIG. 3, coupler 355 may be cylindrical and may have a larger circumference about its longitudinal axis than the circumference of longitudinal member 306 about its longitudinal axis. The larger circumference of coupler 355 may prevent coupler 355 from being pulled through first distal opening 312 into lumen 360 when longitudinal member 306 is pulled proximally. In some examples, coupler 355 may limit the rotation of stapler device 301 about pivot pin 340. Actuation wire 316 may be coupled to an actuation sled 373 via a pin 352 of actuation sled 373 that extends through a slot (not shown) in the bottom of stapler body 308. In some examples, actuation wire 316 is wrapped around pin 352 to couple actuation wire 316 to pin 352. In other examples, actuation wire 316 may be coupled to pin 352 via a crimp tube, glue, and/or any other coupling mechanism known in the art. As shown in FIG. 3, a portion of pin 352 is outside of stapler body 308, and actuation wire 316 is coupled to actuation sled 373 at a position entirely outside of stapler body 308.

FIGS. 4A and 4B illustrate top views of a distal portion of surgical stapler 300. FIG. 4A shows stapler device 301 positioned substantially parallel to longitudinal body 302, and FIG. 4B shows stapler device 301 angled relative to longitudinal body 302. To transition surgical stapler 300 from the position shown in FIG. 4A to the position shown in FIG. 4B, a user may push longitudinal member 306 distally through longitudinal body 302, which may cause stapler device 301 to rotate about pivot pin 340. To transition surgical stapler 300 from the position shown in FIG. 4B to the position shown in FIG. 4A, a user may pull longitudinal member 306 proximally through longitudinal body 302, thus moving body 208 and anvil 310 and pivoting stapler device 301 about pivot pin 340.

FIGS. 5A and 5B illustrate cross-sectional views of two examples of longitudinal members 500, 501, respectively. Each of longitudinal members 500, 501 may have any of the features disclosed herein regarding longitudinal members 206, 306. Longitudinal member 500 may have a cylindrical shape and may be configured to be positioned within a longitudinal body 202, 302. Longitudinal member 501 may include a substantially circular cross-section and a slot portion 502. Slot portion 502 may extend longitudinally the entire length of longitudinal member 501 or may extend longitudinally only a portion of the length of longitudinal member 501. Slot portion 502 may include a curved surface configured to mate with the exterior surface of actuation wire 316. By providing slot portion 502 extending longitudinally through longitudinal member 501, less space is required within lumen 360 to accommodate longitudinal member 501 and actuation wire 316 while allowing longitudinal member 501 and actuation wire 316 to move relative to each other within lumen 360.

FIG. 6 illustrates an exemplary stapler body 608, actuation sled 673, and actuation wire 616 that may be incorporated into any of the stapler devices 201, 301, discussed herein. Stapler body 608 may include a longitudinal slot 675 configured to receive an extension 670 of actuation sled 673. Extension 670 may be T-shaped and may be coupled to a distal end of actuation wire 616. Extension 670 may be configured to couple to actuation wire 616 at a position entirely exterior to stapler body 608. In other examples, actuation wire 616 may be coupled to actuation sled 673 at a position partially within stapler body 608 and/or within longitudinal slot 675. Actuation sled 673 may include two ramp portions 671, 672 positioned within a channel 685 of stapler body 608, and channel 685 may be configured to receive a stapler cartridge 218. Ramp portions 671, 672 may be wide enough such that ramp portions 671, 672, collectively or individually, are wider than the width of longitudinal slot 675. Actuation sled 673 may be pulled proximally through channel 685 when actuation wire 616 is pulled proximally.

FIG. 7 illustrates a distal portion of components of an alternative stapler device including stapler body 708, longitudinal body 702, pivot pin 740, longitudinal member 706, and actuation wire 716. Any of the features discussed herein regarding surgical staplers 200, 300 and stapler body 608 may be included in surgical staplers including components of FIG. 7. Stapler body 708 includes channel 775, and channel 775 receives actuation sled 772. Actuation sled 772 includes ramp 792 and is coupled to actuation wire 716. Actuation wire 716 extends through longitudinal member 706 to a proximal portion of the device. In an embodiment of the stapler utilizing the components of FIG. 7, longitudinal member 706 is not used to rotate stapler body about pivot pin 740, but instead may protect actuation wire 716. In this example, longitudinal member 706 may be flexible and is not required to be sufficiently stiff to move stapler body 708 via proximal or distal movement of longitudinal member 706. A cable 717 may extend through a lumen of longitudinal body 702 and through a lumen opening 721, and a distal end of cable 717 may be rotatably coupled to stapler body 708. For example, as shown in FIG. 7, cable 717 may include a loop portion 718 at a distal end of cable 717. Loop portion 718 may be formed by a distal portion of cable 717 coupled to a proximal portion of cable 717. Loop portion 718 may be formed using a crimp tube 719 or crimp sleeve. In other examples, loop portion 718 may not include crimp tube 719. Loop portion 718 may extend through one or more apertures 781 of stapler body 708. Cable 717 may be sufficiently rigid such that proximal or distal movement of cable 717 may move stapler body 708. In some examples, cable 717 may be a Bowden cable. Cable 717 may be made of stainless steel, nitinol, or any other suitable material. To rotate stapler body 708 about pivot pin 740, a user may move cable 717 proximally or distally. By providing a means to rotate stapler body 708 about pivot pin 740 separate from longitudinal member 706, the amount of force applied by longitudinal member 706 on actuation wire 716 during operation of the stapler may be reduced and may prevent difficulties in moving actuation wire 716 through longitudinal member 706.

Figure 8:
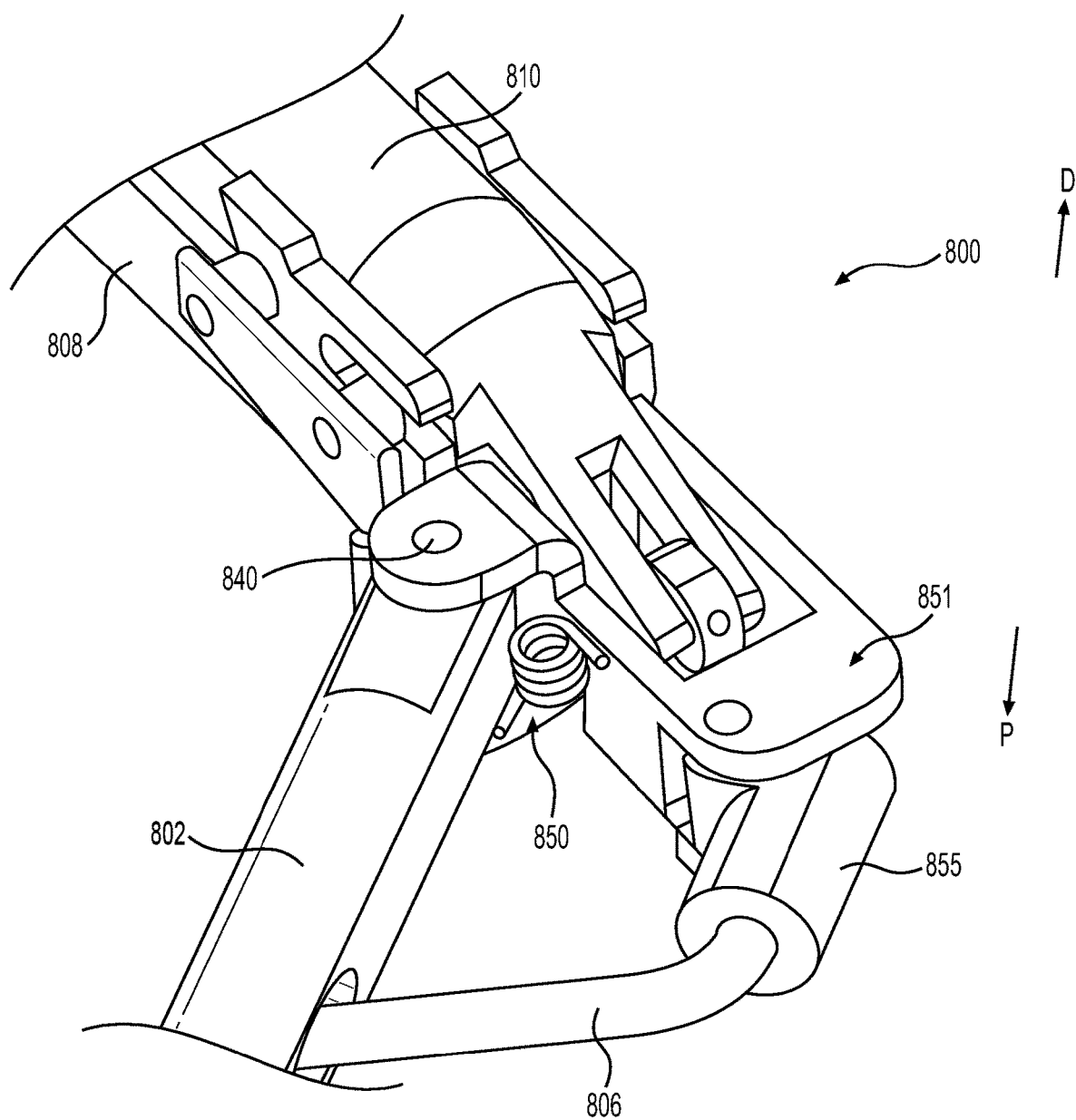
FIG. 8 is a perspective view of an exemplary portion of a surgical stapler, according to aspects of the present disclosure.

FIG. 8 illustrates a distal portion of a surgical stapler 800 including stapler body 808, anvil 810, longitudinal body 802, and longitudinal member 806. Longitudinal member 806 may be coupled to stapler body 808 via a protrusion 851 and a coupler 855 similar to protrusion 333 and coupler 355 of surgical stapler 300. Any of the features described herein regarding surgical staplers 200, 300 may be incorporated in surgical stapler 800. Stapler body 808 may be pivotably coupled to longitudinal body 802, and stapler body 808 may rotate about pivot pin 840. A spring 850 may be coupled to stapler body 808 and longitudinal body 802. Spring 850 may be positioned proximate to pivot pin 840, and in some examples may be coupled to a portion of protrusion 851. Spring 850 may exert a force on stapler body 808 and longitudinal body 802 such that stapler body 808 is spring-biased towards an angled position relative to longitudinal body 802. For example, spring 850 may move stapler body 808 such that the distal end of stapler body 808 moves proximally relative to longitudinal body 802.

A user may pull longitudinal member 806 proximally to pivot stapler body 808 to a position substantially parallel to longitudinal body 802. When a user releases tension applied to longitudinal member 806, stapler body 808 may rotate and a distal end of stapler body 808 may move proximally due to the force applied by spring 850. By providing spring 850, a user may only need to apply tension to longitudinal member 806 in the proximal direction or release tension in longitudinal member 806 to rotate stapler body 808 in either direction (clockwise or counter-clockwise) about pivot pin 840. By providing a mechanism in surgical stapler 800 that does not require a user to push longitudinal member 806 distally to rotate stapler body 808, a user may avoid potential buckling of longitudinal member 806 caused by pushing longitudinal member 806 distally. In other examples, spring 850 may bias stapler body 808 towards a position in which the longitudinal axis of stapler body 808 is substantially parallel to the longitudinal axis of longitudinal body 802.

Each of the aforementioned devices and systems may be used to visualize, couple, and/or cut tissue. In some examples, a user may load a longitudinal body of a stapler device in a working channel of an endoscope by backfeeding the longitudinal body through a distal end of an endoscope working channel to position a portion of the longitudinal body within the working channel. Once the longitudinal body is positioned within a working channel, a handle assembly may be coupled to the proximal end of the longitudinal body. The user may then introduce the endoscope into the patient's body and move the endoscope towards a target area. The user may locate a target area (such as a tumor or other diseased tissue) present in a body lumen of a subject using the endoscope by directly visualizing the target area using an image sensor. Once the user has positioned the endoscope's distal end proximate to a target area, the user may actuate the stapler device to an open position creating a space between the stapler's anvil and body. The user may then position target tissue within the stapler device's active portion, and move the stapler device's anvil and body to a closed position to clamp down on the tissue with the stapler device. The user may then actuate an actuator in order to pull on an actuation wire, thus moving an actuation sled of the stapler device proximally. By moving the actuation sled proximally via an actuator, the user may deploy fasteners into the clamped tissue and against the stapler device's anvil.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device comprising:
    a first body including a proximal end, a distal end, and defining a longitudinal axis, wherein the first body includes a first lumen extending from a proximal portion of the first body to a first lumen opening at a distal portion of the first body, wherein the first body includes a second lumen opening which opens into the first lumen, and wherein the first lumen opening is positioned at an opposite side of the first body from the second lumen opening;
    a fastening device coupled to the distal end of the first body, wherein the fastening device comprises:
        a longitudinal body comprising a cartridge;
        the cartridge configured to hold one or more fasteners;
        an anvil rotatable relative to the cartridge of the longitudinal body;
        a fastener actuator configured to move relative to the cartridge to deploy the one or more fasteners from the cartridge;
        an actuation wire coupled to the fastener actuator, extending through the first body, and positioned at least partially exterior to the longitudinal body, the cartridge, or the anvil; and
    a longitudinal member coupled to a proximal end of the longitudinal body, wherein the longitudinal member and the actuation wire are at least partially positioned within the first lumen.

2. The medical device of claim 1, wherein the longitudinal body is pivotably coupled to the first body.

3. The medical device of claim 1, wherein the longitudinal member includes a longitudinal channel, and wherein the actuation wire is positioned within the longitudinal channel.

4. The medical device of claim 1, wherein the first body includes a first lumen and a second lumen; the longitudinal member is positioned within the first lumen; and the actuation wire is positioned within the second lumen.

5. The medical device of claim 1, wherein the fastener actuator is positioned within a longitudinal slot of the longitudinal body.

6. The medical device of claim 5, wherein the fastener actuator includes at least one ramp portion and an extension portion extending through the longitudinal slot.

7. The medical device of claim 1, further comprising a spring coupled to the first body and the longitudinal body.

8. The medical device of claim 7, wherein the spring is configured to bias the fastening device towards a position in which a longitudinal axis of the longitudinal body is transverse to a longitudinal axis of the first body.

9. The medical device of claim 1, wherein the longitudinal member coupled to a proximal end of the longitudinal body via a coupler, and wherein the coupler has a width larger than the width of the first lumen opening.

10. The medical device of claim 1, further comprising a cable rotatably coupled to the longitudinal body and positioned within the first body, wherein the cable is configured to actuate movement of the fastening device.

11. The medical device of claim 1, wherein the longitudinal body is rotatably coupled to the first body at a position between a proximal end and a distal end of the longitudinal body.

12. The medical device of claim 1, wherein longitudinal member and actuation wire each extend through at least one opening of the first body at a position entirely proximal to the fastening device.

13. A medical device comprising:
    a first body defining a longitudinal axis and including a first lumen; and
    a fastening device rotatably coupled to a distal end of the first body, wherein the fastening device comprises:
        a longitudinal body;
        a cartridge positioned at least partially within the longitudinal body and comprising one or more fasteners;
        an anvil mounted adjacent the cartridge;
        an actuation wire coupled to a fastener actuator at a distal end of the actuation wire, wherein the fastener actuator is positioned within a longitudinal slot of the longitudinal body;
        a second body including a second lumen, wherein the second body is positioned within, movable within, and extends from the first lumen; and
        a cable rotatably coupled to the longitudinal body and extending through the first lumen;
    wherein the actuation wire is positioned within the second lumen; and
    wherein the fastening device is pivotable about the first body when the cable is moved proximally and/or distally.

14. The medical device of claim 13, wherein first body is rotatably coupled to the longitudinal body at a position between a proximal end and a distal end of the longitudinal body.

15. A medical device comprising:
    a first body including a proximal end, a distal end, and defining a longitudinal axis;
    a fastening device coupled to the distal end of the first body, wherein the fastening device comprises:
        a longitudinal body comprising a cartridge;
        the cartridge configured to hold one or more fasteners;
        an anvil rotatable relative to the cartridge of the longitudinal body;
        a fastener actuator configured to move relative to the cartridge to deploy the one or more fasteners from the cartridge;
        an actuation wire coupled to the fastener actuator, extending through the first body, and positioned at least partially exterior to the longitudinal body, the cartridge, or the anvil; and
    a spring coupled to the first body and the longitudinal body, wherein the spring is configured to bias the fastening device towards a position in which a longitudinal axis of the longitudinal body is transverse to a longitudinal axis of the first body.

16. The medical device of claim 15, wherein the longitudinal body is pivotably coupled to the first body.

17. The medical device of claim 15, further comprising a longitudinal member coupled to a proximal end of the longitudinal body.

* * * * *